US00PP36515P3

(12) United States Plant Patent
Muller et al.

(10) Patent No.: US PP36,515 P3
(45) Date of Patent: Mar. 4, 2025

(54) ORANGE TREE NAMED 'Val 1'

(50) Latin Name: *Citrus sinensis*
Varietal Denomination: Val 1

(71) Applicants: Corne Muller, Patensie (ZA); Gert Ferreira, Patensie (ZA)

(72) Inventors: Corne Muller, Patensie (ZA); Gert Ferreira, Patensie (ZA)

( * ) Notice: Subject to any disclaimer, the term of this patent is extended or adjusted under 35 U.S.C. 154(b) by 0 days.

(21) Appl. No.: 18/115,261

(22) Filed: Feb. 28, 2023

(65) Prior Publication Data

US 2024/0292767 P1 Aug. 29, 2024

(51) Int. Cl.
*A01H 5/08* (2018.01)
*A01H 6/78* (2018.01)

(52) U.S. Cl.
USPC ..... Plt./202
CPC ..... *A01H 6/785* (2018.05)

(58) Field of Classification Search
USPC ..... Plt./156, 201, 202
See application file for complete search history.

*Primary Examiner* — Karen M Redden
(74) *Attorney, Agent, or Firm* — R. Scott Kimsey, Esq.

(57) ABSTRACT

A new and distinct navel orange distinguished by production of fruit that combines late-season maturity and a strong orange pigmented rind (UPOV Group 20) with a pink albedo. It further distinguishes itself with a deep orange-red flesh. Flesh, rind, albedo, and juice are deeply pigmented with lycopene'. The new cultivar is a *Citrus sinensis*, useful for commercial fruit production.

6 Drawing Sheets

Latin name: *Citrus sinensis.*
Variety denomination: Val 1.

RELATED APPLICATIONS

Not Applicable.

STATEMENT REGARDING FEDERALLY SPONSORED RESEARCH OR DEVELOPMENT

Not Applicable.

BACKGROUND OF THE INVENTION

The present disclosure relates to a new and distinct variety of navel orange tree, *Citrus sinensis*, originating from a spontaneous branch mutation from a 'Washington' navel (South African Palmer selection) tree (not patented). The variety was discovered by Mr. Corne Muller in a 'Washington' navel orchard in the Gamtoos River Valley, Eastern Cape, South Africa. With the help of Mr. Gert Ferreira, buds from this mutation branch were grafted onto a 'Rough Lemon' (RL) rootstock (not patented) trial on in the Gamtoos River Valley in 2015. Fruit production on these trees commenced in 2019. Asexually propagated plants remain true to the original tree and all characteristics of the fruit and tree were transmitted to subsequent generations.

SUMMARY OF THE INVENTION

The 'Val 1' discovery provides a novel navel orange having the characteristics described and illustrated herein. The variety is a natural, spontaneous mutation of the 'Washington' navel orange. It combines late season maturity, medium-large (75-80 mm) sized fruit, and a strong orange pigmented rind occasionally having a red blush. 'Val 1' is further distinguished by its orange-red pigmented flesh and pink albedo in the vascular bundle. Pigmentation is also visible in bearing wood.

In maturity indexing trials in the Gamtoos River Valley, 'Val 1' matured between three and four weeks later than the current benchmark red navel, 'Cara Cara' (not patented), and four weeks later than the 'Washington' navel. In the two years immediately prior to this writing, 'Val 1' matured at the same time as the 'Lane Late' navel (not patented). 'Val 1' is distinguished from this late maturing navel by being red-fleshed with a less pronounced navel end.

The fruit of 'Val 1' is suitable for the fresh fruit and juice markets.

BRIEF DESCRIPTION OF THE ILLUSTRATIONS

The accompanying photographs consist of color photographs as follows.

DETAILED DESCRIPTION OF THE INVENTION

Figure 1:
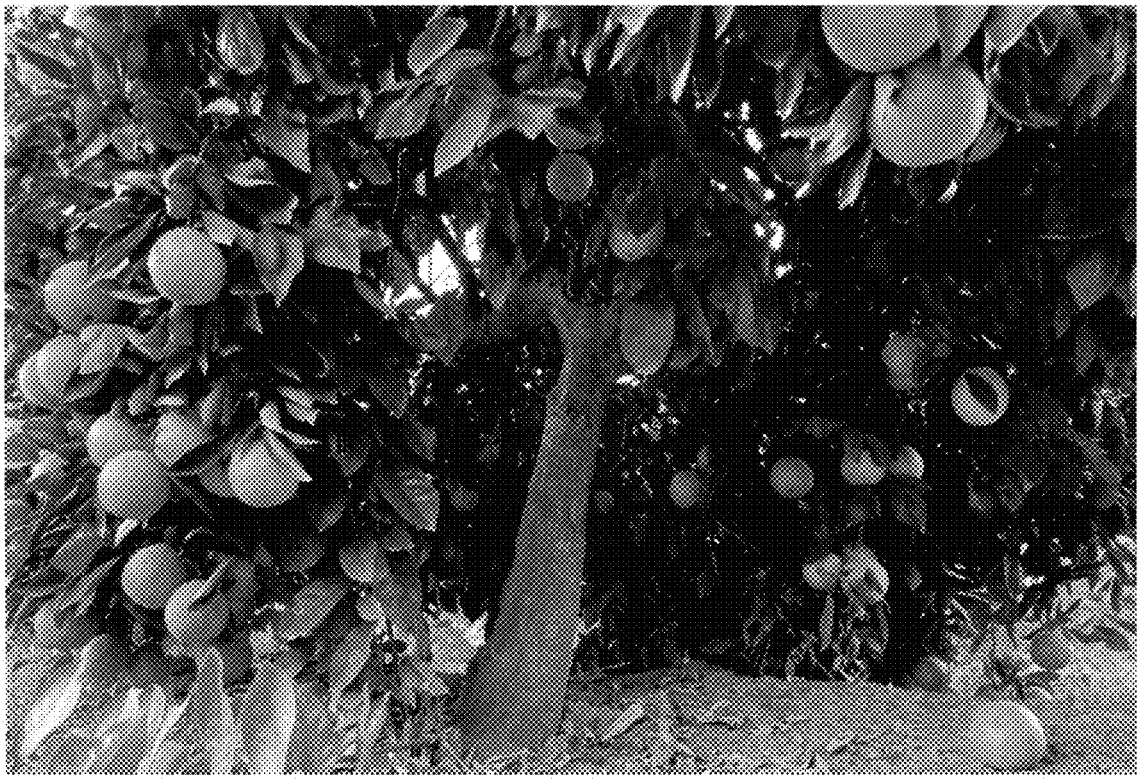
FIG. 1 depicts a seven-year old top-grafted 'Val 1' tree on 'Rough Lemon' rootstock.
Figure 2:
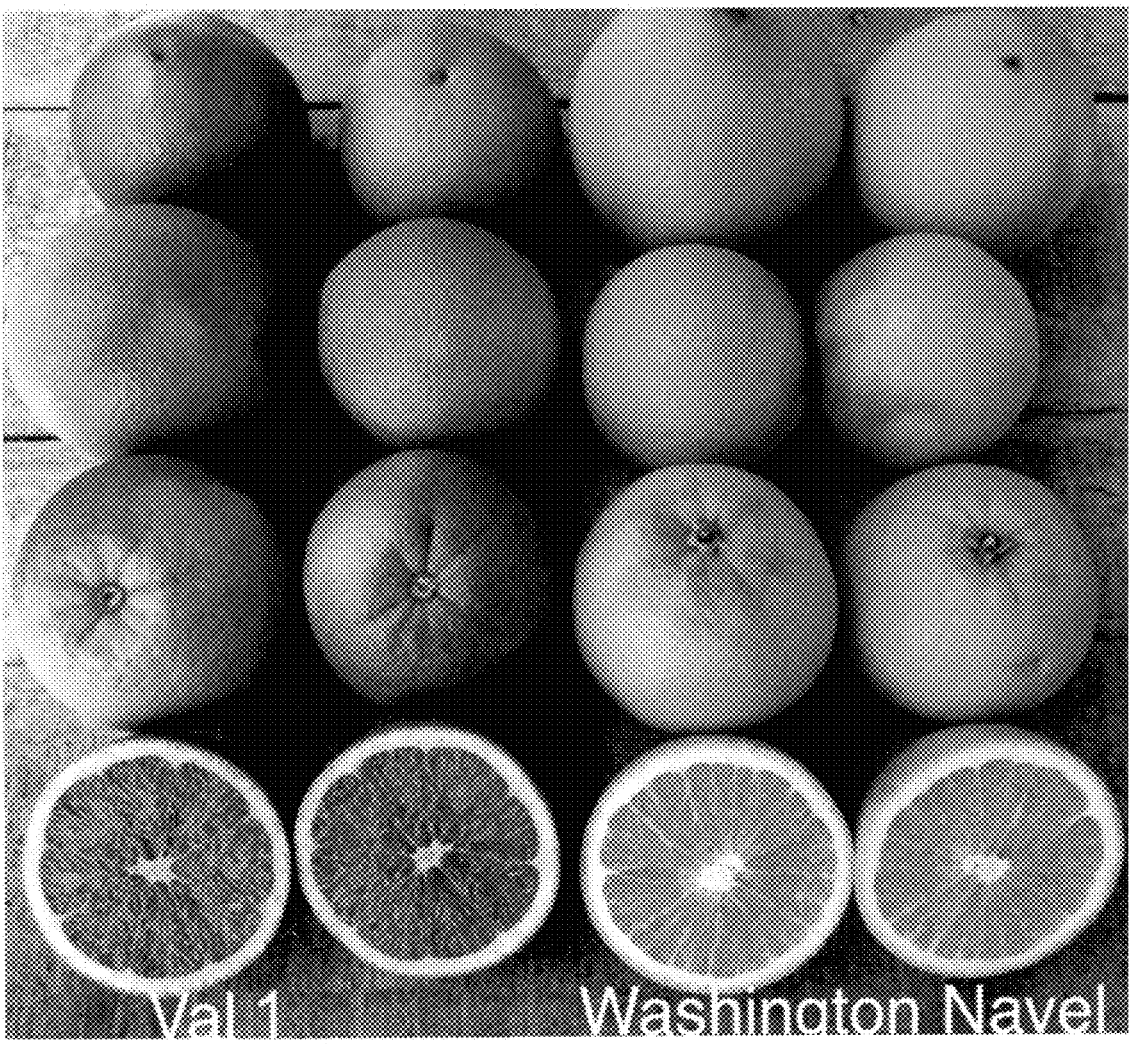
FIG. 2 shows a comparison of the parent 'Washington' navel (right) and the 'Val 1' mutation (left).
Figure 3:
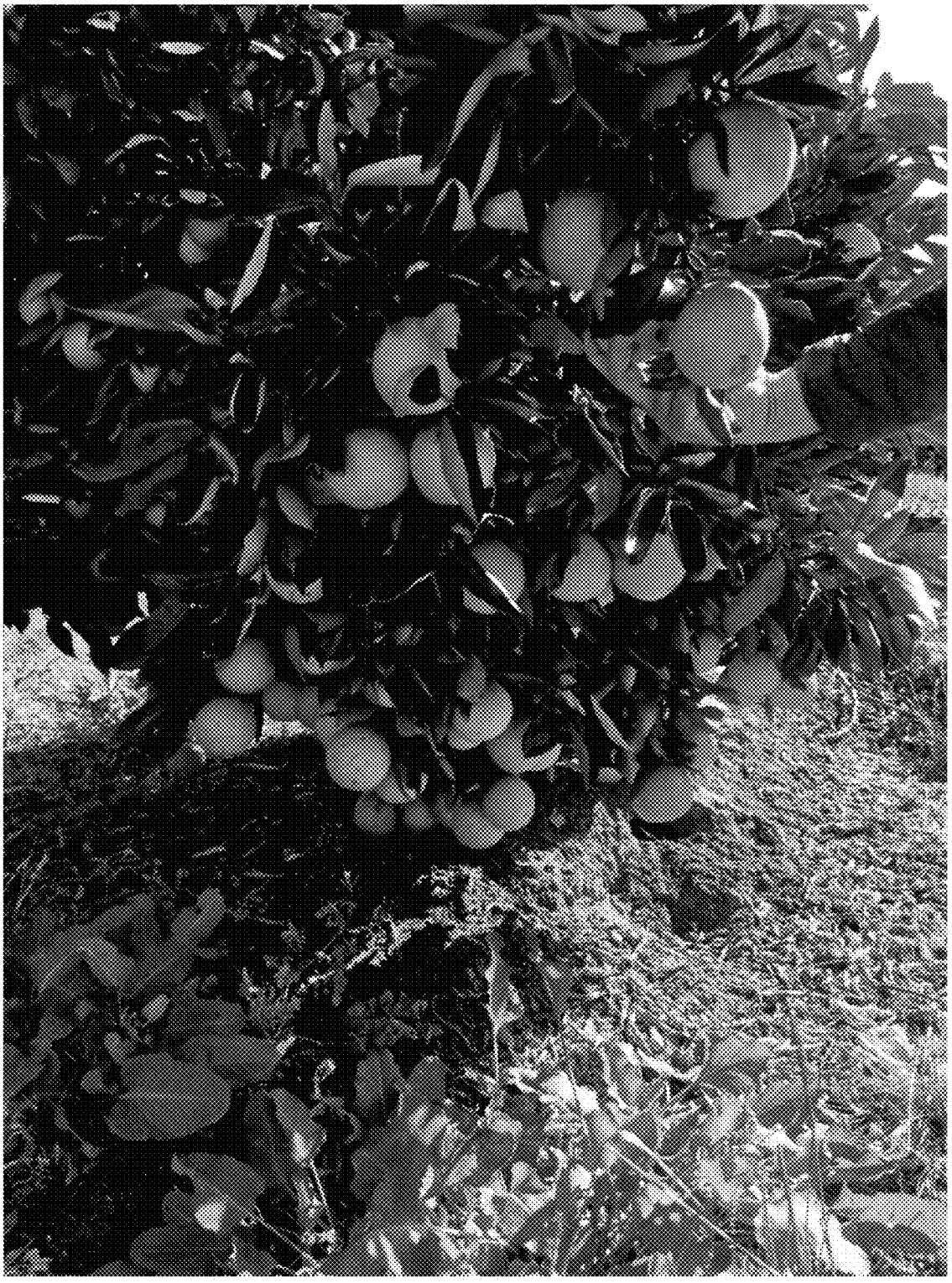
FIG. 3 depicts 'Val 1' fruit on a seven-year old tree.
Figure 4:
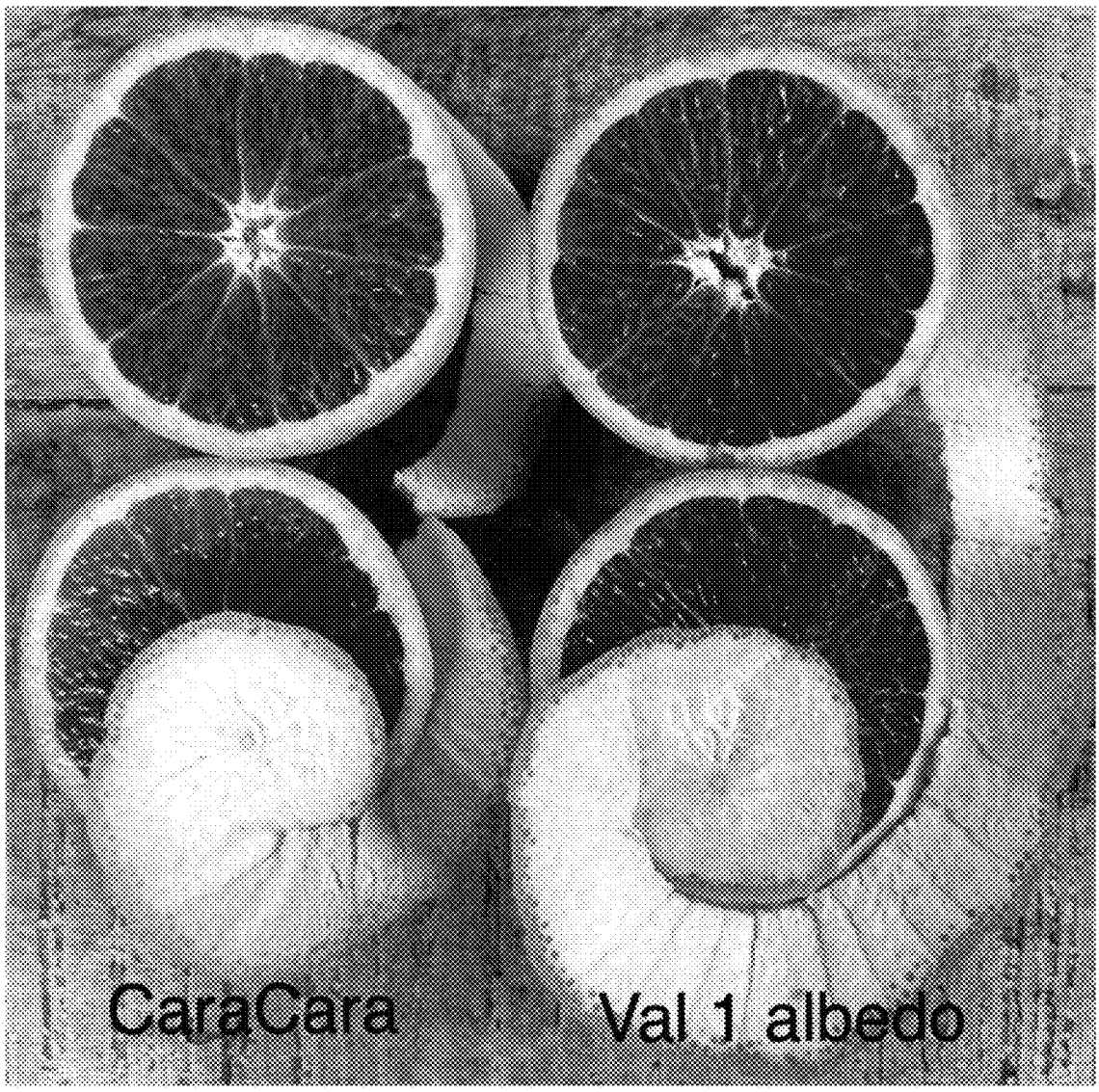
FIG. 4 shows 'Val 1' albedo and flesh color (right) in comparison with the reference 'Cara Cara' navel variety (left).
Figure 5:
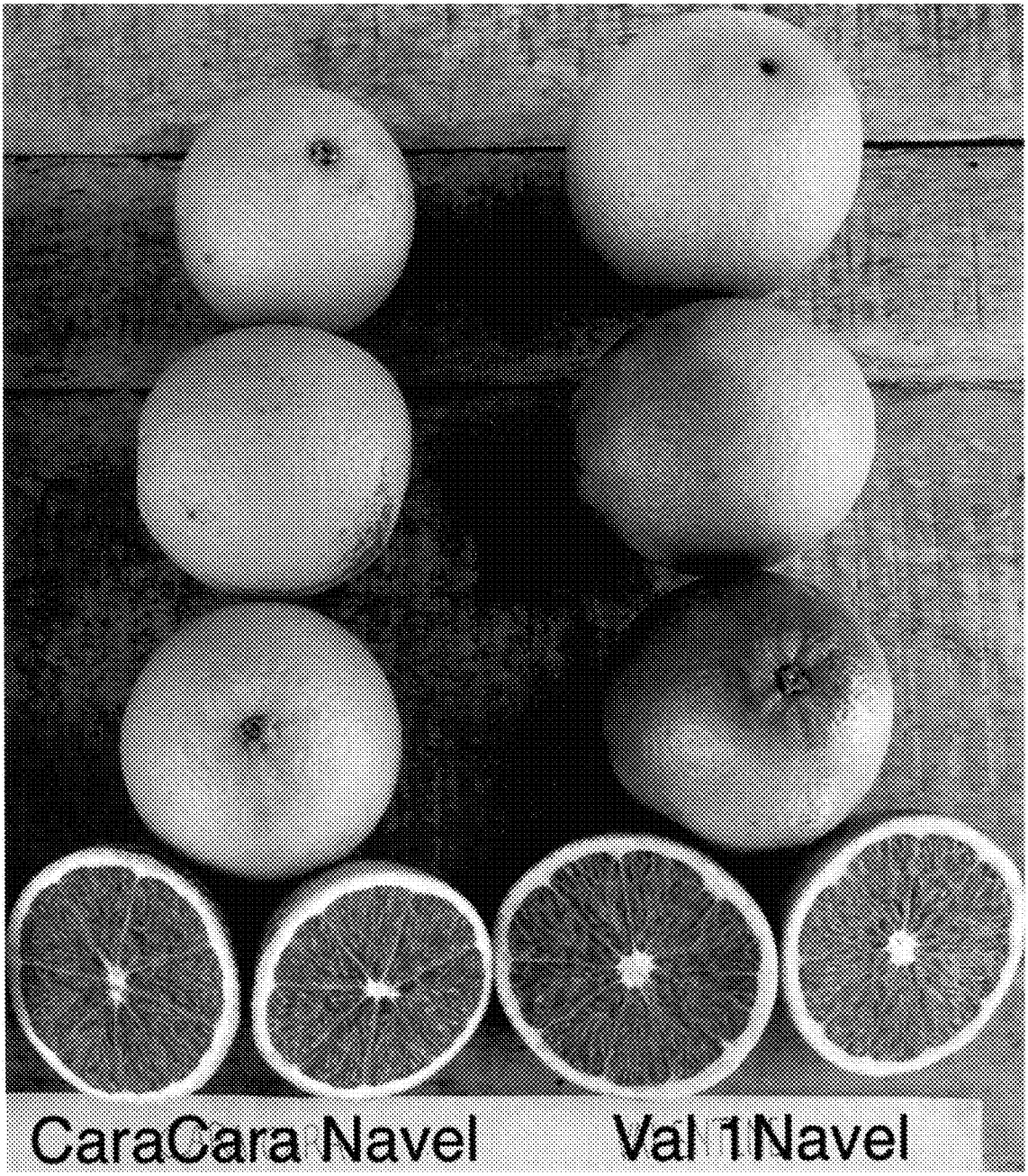
FIG. 5 shows 'Val 1' rind and flesh color (right) in comparison with the reference 'Cara Cara' navel variety (left).
Figure 6:
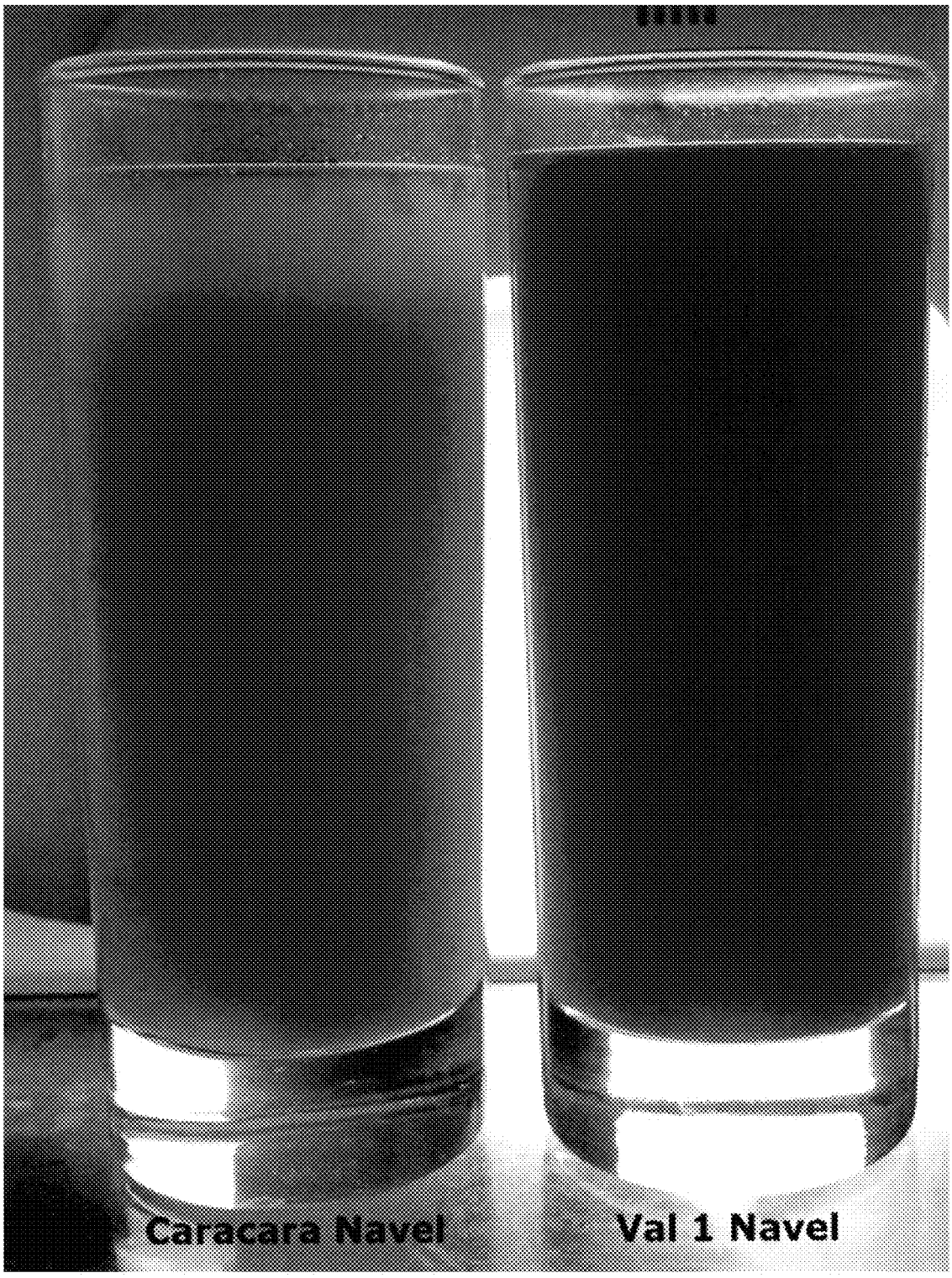
FIG. 6 shows 'Val 1' juice color (right) in comparison to the 'Cara Cara' navel variety (left).

Referring to the botanical description of the new and distinct variety, the following traits and characteristics have been observed in representative plants of the new variety grown in the in the Gamtoos River Valley, Eastern Cape, South Africa. Evaluation began on the top-grafted daughter trees in 2019. Tree size, growth, fruit production, and internal and external fruit characteristics have been compared to the two reference varieties: the 'Washington' navel parent and the 'Cara Cara' navel.

COMPARISON TO PARENT VARIETY AND COMMERCIAL REFERENCE

Trees of the new 'Val 1' cultivar are similar in many horticultural characteristics to trees of the parent 'Washington' navel. 'Val 1' differs from the 'Washington' navel, among other ways described below, as follows:

1. 'Val 1' leaves are narrower, shorter and generally darker, and the ratio of length to width is larger than in the 'Washington' navel.
2. The flesh of the 'Val 1' fruit is red-pigmented, due to lycopene, in comparison to the yellow-orange flesh of the 'Washington' navel fruit. The rind of the fruit is a darker orange-red than 'Washington'.

'Val 1' initially showed compact growth and moderate vigor in comparison with both 'Washington' and 'Cara Cara' navels. After disease eradication by shoot-tip grafting, however, 'Val 1' trees showed vigor similar to that of disease-free 'Washington' and 'Cara Cara' trees grown at the same site. Although the trees assessed were not yet fully grown, growth rates at the time of assessment were similar to those of 'Washington' and 'Cara Cara'.

Crop production was observed to be consistently heavy in 'Val 1' over the first three years of bearing, with the crop in 2022 being particularly heavy and out-yielding 'Cara Cara'. The 'Val 1' fruit sizes during these heavy-yield years range between 75 mm to 80 mm but are expected to be similar in size to the fruits of 'Washington' (78 mm to 89 mm) and 'Cara Cara' (79 mm to 90 mm) during normal-yield crop years. The fruit of 'Val 1' has a round shape similar to that of both 'Washington' and 'Cara Cara'. The fruit of 'Val 1' is entirely seedless, as with 'Washington' and 'Cara Cara', and peeling of the rind is the same among all three varieties.

With respect to the 'Cara Cara' navel reference variety, 'Val 1' consistently produces fruit flesh with a darker orange-red pigment than the red-pink of the 'Cara Cara'. The 'Val 1' rind is darker in color than 'Cara Cara' and some of the fruit shows a red-blushed rind absent in the 'Cara Cara'. The albedo of 'Val 1' shows pink pigmentation, whereas the 'Cara Cara' navel has a white albedo. Further, pigmentation is present in the wood of the 'Val 1' and absent in the wood of 'Cara Cara'.

With respect to internal quality, fruit from seven-year old 'Val 1' trees was assessed in comparison to fruit from twenty-two year old 'Washington' and twenty-year old 'Cara Cara' trees grown at the same location. The trees were assessed for juice percentage, Brix, acid, and average seed content, with the results as shown in Table 1.

TABLE 1

Comparison of 'Val 1', 'Washington', and 'Cara Cara'

| Date Assessed | Selection | Root-stock | Juice % | Brix | Acid | Ratio | Avg. Seed |
|---|---|---|---|---|---|---|---|
| 21 JUN. 22 | 'Val 1' | RL | 54.9 | 12 | 1.63 | 7.4 | 0 |
| 21 JUN. 22 | 'Washington' | RL | 43.6 | 11.8 | 1.05 | 11.2 | 0 |

TABLE 1-continued

Comparison of 'Val 1', 'Washington', and 'Cara Cara'

| Date Assessed | Selection | Root-stock | Juice % | Brix | Acid | Ratio | Avg. Seed |
|---|---|---|---|---|---|---|---|
| 21 JUN. 22 | 'Cara Cara' | RL | 46.2 | 11 | 1.25 | 8.8 | 0 |
| 16 JUL. 22 | 'Val 1' | RL | 54.1 | 12.94 | 1.28 | 10.1 | 0 |
| 16 JUL. 22 | 'Cara Cara' | RL | 51 | 11.95 | 0.87 | 13.74 | 0 |

Navel varieties in South Africa are considered to have reached internal maturity suitable for export upon reaching a Brix:Acid ratio of 10.5. As shown in Table 1, the 'Washington' navel reached maturity first, with a Brix:Acid ratio of 11.2 on Jun. 21, 2022. 'Cara Cara' and 'Val 1' had both failed to reach the required maturity at that time, with Brix:Acid ratios of 8.8 and 7.4 respectively. The high acidity of 'Val 1', coupled with a good Brix measurement, indicates that 'Val 1' will mature later than the reference varieties. By Jul. 16, 2022, 'Cara Cara' reached the desired maturity, with a Brix:Acid ratio of 13.74, whereas 'Val 1' still hadn't reached the desired maturity level. On both dates, however, 'Val 1' had higher Brix scores than either 'Washington' or 'Cara Cara'. The data supports a 'Val 1' maturity time of four to five weeks after 'Washington' and three to four weeks after 'Cara Cara'.

BOTANICAL DESCRIPTION

Color codes are taken from The Royal Horticultural Society Colour Chart, 5$^{th}$ edition (2007).

Tree:

Age and location of tree described: Approximately 8 years; Gamtoos River Valley, Eastern Cape, South Africa.

*Habit*.—Upright.
*Vigor*.—Medium to strong.
*Tree height*.—3.14 m.
*Tree spread*.—3 m.
*Diameter of scaffold branches at breast height*.—8 cm.
*Diameter of trunk at breast height*.—12 cm.
*Pollination requirement*.—None.
*Disease resistance/susceptibility*.—No distinct resistance or susceptibility observed.

Trunk characteristics:

*Spines*.—Absent.

Leaves:

*Length of blade*.—Average 91.7 mm.
*Width of blade*.—Average 38.9 mm.
*Ratio of length to width*.—Average 1:2.35.
*Leaf arrangement*.—Alternate.
*Venation*.—Pinnate.
*Shape of blade in cross-section*.—Intermediate.
*Emargination at tip*.—Present.
*Apex*.—Acute.
*Leaf blade*.—Twisting — Absent or weak.
*Leaf blade*.—Blistering — Absent or weak.
*Undulation of margin*.—Absent or weak.
*Emargination at tip*.—Present.
*Blade color*.—Medium green (136A) upper surface.
*Leaf texture*.—Waxy; smooth.
*Stipule*.—Present; Average 1 mm length.
*Petiole length*.—Average 14 mm.
*Petiole wings*.—Present; Average 3.6 mm width.

Flowers:

*Petal length*.—Average 15.8 mm.
*Petal width*.—Average 6.2 mm.

*Ratio*.—Length/Width of Petal — Average 1:2.548.
*Diameter of calyx*.—Average 6.4 mm.
*Timing of buds*.—Early October in the Eastern Cape Province of South Africa.

Reproduction organs:
*Stamen filament length*.—Average 9.6 mm.
*Basal union of stamens*.—Present.

Anthers:
*Style*.—Arched; Average 7.8 mm length.

Fruit:
*Color exocarp*.—Strong orange (24A to 24B); variegation absent.
*Color of albedo*.—Pink (62B).
*Flesh color*.—Orange-red (34B to 34C).
*Specks in flesh*.—Absent.
*Bitterness of flesh*.—Absent.
*Length*.—Average 73.4 mm.
*Diameter*.—Average 76.7 mm.
*Ratio*.—Length/Diameter of fruit — Average 1:0957.
*General shape*.—Proximal part (excluding neck, collar, and depression at stalk end), slightly rounded; distal part (excluding nipple, bulging of navel, and depression at distal end), slightly rounded; broadest part at middle.
*Fruit neck*.—Absent.
*Stalk end depression*.—Present; Shallow.
*Stalk end radial grooves*.—Many (average 6.9); average 15.5 mm length.
*Coloration at stalk attachment*.—Anthocyanine.
*Fruit collar*.—Absent.
*Distal end depression*.—Absent.
*Depth of stalk end depression*.—Average 2.42 mm.
*Distal end radial grooves*.—Absent.
*Areola*.—Absent.
*Diameter stylar scar*.—Average 1.8 mm.
*Persistence of style*.—None.
*Naval opening*.—Occasionally present; average diameter 5.05 mm; absent or weak to intermediate bulging.
*Skin/rind texture*.—Smooth to medium.
*Rind*.—Average 4.05 mm thickness; medium strength.
*Oil glands*.—Present; weak to medium conspicuousness; pitting and pebbling present; sparse density of pitting; medium density and degree of pebbling.
*Fruit core*.—Average 9.7 mm diameter; very dense — average 97.5% filling.
*Rudimentary segments*.—Absent or weak.
*Number of well*.—developed segments.—Average 10.4.
*Bicolored segment flesh* (*strands excluded*).—Present.
*Segment wall strength*.—Medium.
*Coherence of adjacent segment walls*.—Medium.
*Fruit juiciness*.—Low to medium.
*Fruit total soluble solids*.—High.
*Fruit strength of fiber*.—Medium.
*Juice vesicles*.—Short to medium length; medium thickness; medium coherence; medium conspicuousness of walls.
*Juiciness*.—Low to medium.
*Total soluble solids*.—Average 12.1%.
*Strength of fibre*.—Medium.
*Fruit parthenocarpy*.—Present.
*Seeds*.—Absent to few.
*Presence of navel* (*viewed internally*).—Occasionally present to always present.
*Size of navel* (*viewed internally*).—Small.
*Stability of fruit*.—Stable; excellent storage life.
*Winter hardiness*.—Similar to that of parental 'Washington' cultivar.
*Fruit productivity*.—Approximately 50-55 tons/Ha.
*Time of maturity for fruit consumption*.—Beginning of June to middle of July in the Gamtoos River Valley, Eastern Cape, South Africa.

The new variety exhibits the characteristics shown and described when grown under the ecological conditions prevailing in the Gamtoos River Valley, Eastern Cape, South Africa. It is understood that variations of the usual magnitude and characteristics may be expected as a result of changes in growing conditions, location, fertilization, pruning, pest control, and horticultural management practices.

The invention claimed is:

1. A new and distinct variety of orange tree named 'Val 1' as illustrated and described herein.

* * * * *